(12) United States Patent
Carney et al.

(10) Patent No.: US 9,694,186 B2
(45) Date of Patent: Jul. 4, 2017

(54) DUAL CHAMBER TIMING FOR LEADLESS PACEMAKERS USING INFREQUENT ATRIAL SIGNALS AND VENTRICULAR CONTRACTIONS

(71) Applicant: Medtronic, Inc., Minneapolis, MN (US)

(72) Inventors: James K. Carney, Roseville, MN (US); Saul E. Greenhut, Aurora, CO (US)

(73) Assignee: Medtronic, Inc., Minneapolis, MN (US)

( * ) Notice: Subject to any disclaimer, the term of this patent is extended or adjusted under 35 U.S.C. 154(b) by 166 days.

(21) Appl. No.: 14/510,558

(22) Filed: Oct. 9, 2014

(65) Prior Publication Data

US 2016/0067490 A1    Mar. 10, 2016

Related U.S. Application Data

(60) Provisional application No. 62/047,315, filed on Sep. 8, 2014.

(51) Int. Cl.
| | | |
|---|---|---|
| *A61N 1/368* | (2006.01) | |
| *A61N 1/365* | (2006.01) | |
| *A61N 1/375* | (2006.01) | |
| *A61N 1/372* | (2006.01) | |

(52) U.S. Cl.
CPC ......... *A61N 1/368* (2013.01); *A61N 1/36592* (2013.01); *A61N 1/3756* (2013.01); *A61N 1/37276* (2013.01); *A61N 1/37288* (2013.01)

(58) Field of Classification Search
CPC .... A61N 1/365; A61N 1/368; A61N 1/36592; A61N 1/3682

USPC ................................................ 607/25, 17–18
See application file for complete search history.

(56) References Cited

U.S. PATENT DOCUMENTS

| | | |
|---|---|---|
| 7,565,195 B1 | 7/2009 | Kroll et al. |
| 7,630,767 B1 | 12/2009 | Poore et al. |
| 2004/0147973 A1 | 7/2004 | Hauser |
| 2006/0135999 A1* | 6/2006 | Bodner .................. A61N 1/056 607/4 |
| 2012/0109236 A1 | 5/2012 | Jacobson et al. |
| 2013/0103109 A1 | 4/2013 | Jacobson |

(Continued)

FOREIGN PATENT DOCUMENTS

WO      2006065394 A1    6/2006

OTHER PUBLICATIONS

C00003072.WOU3 (PCT/US2015/042327) PCT Notification of Transmittal of the International Search Report and the Written Opinion of the International Searching Authority, mailed Oct. 14, 2015, 10 pages.

*Primary Examiner* — Carl H Layno
*Assistant Examiner* — Jon Eric C Morales

(57) ABSTRACT

A method for adjusting a pacing rate in a dual-chamber, leadless pacemaker implanted in a heart may involve determining, with a leadless atrial pacemaker implanted in an atrium of the heart, that an intrinsic atrial contraction rate of the atrium is faster than a ventricular contraction rate, transmitting a first signal from the atrial pacemaker to a leadless ventricular pacemaker implanted in a ventricle of the heart to increase a ventricular pacing rate of the ventricular pacemaker, receiving the transmitted first signal with the ventricular pacemaker, and increasing the ventricular pacing rate, based on the received first signal.

20 Claims, 5 Drawing Sheets

(56) References Cited

U.S. PATENT DOCUMENTS

| | | |
|---|---|---|
| 2013/0123872 A1 | 5/2013 | Bornzin et al. |
| 2013/0138006 A1 | 5/2013 | Bornzin et al. |
| 2013/0325081 A1 | 12/2013 | Karst et al. |
| 2014/0121719 A1 | 5/2014 | Bonner et al. |
| 2014/0121720 A1 | 5/2014 | Bonner et al. |
| 2015/0335894 A1* | 11/2015 | Bornzin ............... A61N 1/3682 607/18 |

* cited by examiner

DUAL CHAMBER TIMING FOR LEADLESS PACEMAKERS USING INFREQUENT ATRIAL SIGNALS AND VENTRICULAR CONTRACTIONS

CROSS-REFERENCE TO RELATED APPLICATION

This application claims priority to U.S. Provisional Application Ser. No. 62/047,315, filed on Sep. 8, 2014 and entitled "DUAL CHAMBER TIMING FOR LEADLESS PACEMAKERS USING INFREQUENT ATRIAL SIGNALS AND VENTRICULAR CONTRACTIONS," the content of which is incorporated by reference herein in its entirety.

TECHNOLOGICAL FIELD

This disclosure relates to cardiac pacing devices and methods. More specifically, the disclosure relates to techniques for adjusting pacing timing in a dual-chamber, leadless pacemaker system.

BACKGROUND

Leadless pacemakers are used to sense electrical activity and/or deliver therapeutic pacing pulses to the heart. For some patients, one atrial pacemaker may be used in one atrium of the heart. In other patients, multiple leadless pacemakers may be used in at least one atrium and at least one ventricle of the heart. Each leadless pacemaker device typically includes two or more electrodes on its outer housing to deliver therapeutic electrical pulses and/or sense intrinsic depolarizations of the heart. Each leadless pacemaker may be positioned within a chamber of the heart and, in some examples, may be anchored to a wall of the heart via a fixation mechanism.

In dual-chamber, leadless pacemaker systems, two or more pacemakers in two or more chambers of the heart must be able to pace the chambers in synchronous fashion. At the same time, sending timing signals from one leadless pacemaker in one chamber of the heart to another leadless pacemaker in another chamber of the heart, as well as receiving and processing the delivered signals with the receiving pacemaker(s), consumes large amounts of battery power, thus decreasing the useful life of the leadless pacemaker devices.

Therefore, it would be desirable to have a dual-chamber, leadless pacemaker system that maintains a desired timing of its pacing pulses with minimal communication between pacemakers in different heart chambers. Such a system would help reduce battery consumption and thus extend the useful life of the system, while still achieving a desired pacing timing.

SUMMARY

The dual-chamber, leadless pacing systems of the present disclosure generally include at least one atrial pacing device (or "atrial pacemaker" or "atrial device") and at least one ventricular pacing device (or "ventricular pacemaker" or "ventricular device"). Although the systems described herein are often referred to as "dual-chamber" systems, these systems may, in some embodiments, include pacemakers for use in more than two chambers of the heart—e.g., two atria and one ventricle, one atria and two ventricles, or two atria and two ventricles.

The atrial pacing device of the present disclosure is configured for implantation within an atrium of a patient's heart. The atrial device may pace the atrium, sense intrinsic atrial electrical activity, and detect ventricular activation. The atrial device may be configured to detect ventricular activation by detecting ventricular electrical activity and/or mechanical contraction of the ventricles. The atrial device may control the timing of pacing pulses delivered to the atrium based on when atrial and ventricular activations are detected.

In dual-chamber systems, the atrial device operates along with at least one ventricular pacing device that is configured for implantation within a ventricle of the patient's heart. The ventricular device may be configured to sense ventricular depolarizations and to pace the ventricle. In some examples, the ventricular device may be programmed to a backup pacing rate (e.g., less than the atrial pacing rate), such that the ventricular device paces only in situations in which atrial depolarizations do not precipitate ventricular depolarizations—e.g., during AV block. This backup pacing rate may be a fixed rate, for example 50 pulses per minute ("ppm"), or may alternatively track a certain number of ppm below the ventricular intrinsic rate (for example, 10 ppm below the ventricular intrinsic rate). In addition, the ventricular device may be configured such that, after a specified number of ventricular paces at the backup rate, the ventricular pacing rate switches to a rate determined by a sensor, called the ventricular sensor rate.

Various embodiments and details of leadless pacing systems are described in U.S. Patent Application Pub. No. 2014/0121720, titled "Leadless Pacemaker System," filed Oct. 31, 2012, the full disclosure of which is hereby incorporated by reference. In many cases, the leadless pacing system described herein may coordinate pacing of the heart based on sensed cardiac electrical and/or mechanical activity most or all of the time. In this manner, the atrial device and the ventricular device may operate independently from one another, in the sense that operation of the atrial and ventricular devices may depend on sensed cardiac activity (electrical or mechanical) and may not need to rely on wireless communication. In some instances, however, as described further below, an atrial pacemaker device will communicate with a ventricular pacemaker device to help maintain synchronous pacing of the heart. Rather than sending signals continuously from an atrial device to a ventricular device, the system and method described herein provide for signaling only as needed to maintain synchronous pacing. The system and method described below thus provide for limited communication between devices, to help keep the devices pacing in a synchronous fashion without using large quantities of battery power.

In one aspect of the present disclosure, a method for adjusting a pacing rate in a dual-chamber, leadless pacemaker system implanted in a heart may involve determining, with a leadless atrial pacemaker implanted in an atrium of the heart, that an intrinsic atrial contraction rate of the atrium is faster than a ventricular contraction rate, transmitting a first signal from the atrial pacemaker to a leadless ventricular pacemaker implanted in a ventricle of the heart to increase a ventricular pacing rate of the ventricular pacemaker, receiving the transmitted first signal with the ventricular pacemaker, and increasing the ventricular pacing rate, based on the received first signal. In some embodiments, the atrial contraction rate is a rate of contractions of the atrium per minute, and the ventricular contraction rate is a rate of contractions of the ventricle per minute.

Optionally, the method may further include, after the transmitting step, determining, with the atrial pacemaker, that the intrinsic atrial contraction rate is still faster than the ventricular contraction rate, transmitting a second signal from the atrial pacemaker to the ventricular pacemaker to increase the ventricular pacing rate, receiving the transmitted second signal with the ventricular pacemaker, and increasing the ventricular pacing rate, based on the received second signal. The method may involve repeating the determining, transmitting, receiving and increasing steps until the ventricular contraction rate exceeds the intrinsic atrial contraction rate. The method may also optionally include determining, with the atrial pacemaker, that the ventricular contraction rate exceeds the intrinsic atrial rate, and sending pacing pulses from the atrial pacemaker to the atrium to cause the atrium to contract at an atrial pacing rate that approximates the ventricular contraction rate. The method may also include maintaining the ventricular pacing rate and the atrial pacing rate over time, where the atrial pacing rate and the ventricular pacing rate are faster than the atrial intrinsic rate.

In some instances, the method may involve determining, with the ventricular pacemaker, that a threshold ventricular pacing rate has been reached, and discontinuing any further increases in the ventricular pacing rate. The method may also include determining, with the ventricular pacemaker, that no signal has been received from the atrial pacemaker for a predetermined amount of time, and decreasing the ventricular pacing rate. In some embodiments, for example, the ventricular pacing rate may be decreased by a predetermined decrement of at least 2 ppm ("pulses per minute") and not more than 10 ppm. In some embodiments, the predetermined decrement for decreasing the ventricular pacing rate may be smaller than a predetermined increment for increasing the ventricular pacing rate. The method may additionally include, after the decreasing step, determining, with the ventricular pacemaker, that no signal has been received from the atrial pacemaker for another predetermined amount of time, and decreasing the ventricular pacing rate again by the predetermined decrement. The determining and decreasing steps may be repeated until the ventricular pacing rate reaches the ventricular sensor rate or senses ventricular depolarizations, indicating that the AV node is no longer blocked. In various embodiments, the ventricular pacing rate may be increased by a predetermined increment of at least 2 ppm and not more than 10 ppm. In some embodiments, the ventricular pacing rate may be increased from a current rate to a next higher predetermined level of pacing rates.

The method may also include, before the determining step, sensing, with the atrial pacemaker, multiple signals indicative of multiple contractions of the ventricle, and determining the ventricular contraction rate from the multiple signals. Sensed signals may include, for example, far-field R-waves and/or heart sounds. The determining step may involve determining that a predetermined percentage of atrial events (atrial paces and atrial senses) from the atrial pacemaker are atrial senses. In some embodiments, the transmitting step is only performed if at least the predetermined percentage of atrial events from the atrial pacemaker is atrial senses.

In some embodiments, the transmitting step may involve transmitting the first signal in a form such as an acoustic signal, a trans-cardiac conductance signal, an optical signal and a radiofrequency signal.

In another aspect of the present disclosure, a non-transitory, computer-readable storage medium may store a set of instructions that cause a dual-chamber, leadless pacemaker system implanted in a heart to perform a method. The method may involve determining, with a leadless atrial pacemaker implanted in an atrium of the heart, that an intrinsic atrial contraction rate of the atrium is faster than a ventricular contraction rate, transmitting a first signal from the atrial pacemaker to a leadless ventricular pacemaker implanted in a ventricle of the heart to increase a ventricular pacing rate of the ventricular pacemaker, receiving the transmitted first signal with the ventricular pacemaker, and increasing the ventricular pacing rate, based on the received first signal. The method may have any of the features described above.

In another aspect of the present disclosure, an implantable, dual-chamber, leadless pacemaker system may include an atrial leadless pacemaker and a ventricular leadless pacemaker. The atrial leadless pacemaker may include a sensing module configured to sense signals indicative of ventricular contractions, a processing module configured to determine whether an intrinsic atrial contraction rate is greater than a ventricular contraction rate, and a communication module configured to transmit a signal to a ventricular leadless pacemaker to increase a ventricular pacing rate in response to instructions from the processing module to increase the ventricular pacing rate. The ventricular leadless pacemaker may include a sensing module configured to receive the transmitted signal from the atrial pacemaker and a processing module configured to increase the ventricular pacing rate according to the received signal, to determine when no signal has been received from the atrial pacemaker for a predetermined amount of time, and to decrease the ventricular pacing rate when no signal has been received from the atrial pacemaker for the predetermined amount of time.

In some embodiments, the sensing module of the atrial pacemaker is configured to sense far-field R-waves and/or heart sounds. In some embodiments, the processing module of the atrial pacemaker is further configured to determine that the ventricular contraction rate exceeds the intrinsic atrial contraction rate and discontinue transmission of signals from the atrial pacemaker to the ventricular pacemaker. The processing module of the atrial pacemaker may be further configured to begin pacing the atrium at an atrial pacing rate that is faster than the intrinsic atrial rate and that at least approximately matches the ventricular pacing rate. The processing module of the atrial pacemaker may also be configured to detect atrial tachyarrhythmias. For example, the processing module of the atrial pacemaker may be configured to sense when the atrial intrinsic rate exceeds a threshold, which may be defined by the processing module as tachyarrhythmia. In one embodiment, for example, the threshold may be 180 beats per minute.

The processing module of the ventricular pacemaker may be configured to increase and decrease the ventricular pacing rate by predetermined increments and decrements of at least 2 ppm and no more than 10 ppm. In some embodiments, the processing module of the ventricular pacemaker may be configured to increase the ventricular pacing rate by a predetermined increment and decrease the ventricular pacing rate by a predetermined decrement that is less than the predetermined increment. In other embodiments, the processing module of the ventricular pacemaker may be configured to increase and decrease the ventricular pacing rate between predetermined, quantized levels. These levels may be evenly spaced (e.g. 70 ppm, 75 ppm, 80 ppm) or unevenly spaced (e.g. 70 ppm, 75 ppm, 85 ppm). In other embodiments, the processing module of the ventricular pacemaker may be configured to increase and decrease the ventricular pacing rate based on predetermined increments or decrements of the time interval between ventricular paces. Optionally, the processing module of the ventricular pacemaker may be further configured to determine that a threshold ventricular pacing rate has been reached and discontinue increasing the ventricular pacing rate.

The processing module of the atrial pacemaker may be further configured to determine that a predetermined percentage of atrial events are sensed intrinsic contractions and to only send instructions to the transmitting module to transmit the signal to the ventricular pacemaker if at least the predetermined percentage of events is intrinsic contractions. The communication module of the atrial pacemaker may be configured to send the signal from the atrial pacemaker to the ventricular pacemaker in a form selected from the group consisting of an acoustic signal, a trans-cardiac conductance signal, an optical signal and a radiofrequency signal.

These and other aspects and embodiments of the disclosure are described in greater detail below, in reference to the attached drawing figures.

DETAILED DESCRIPTION

Figure 1:
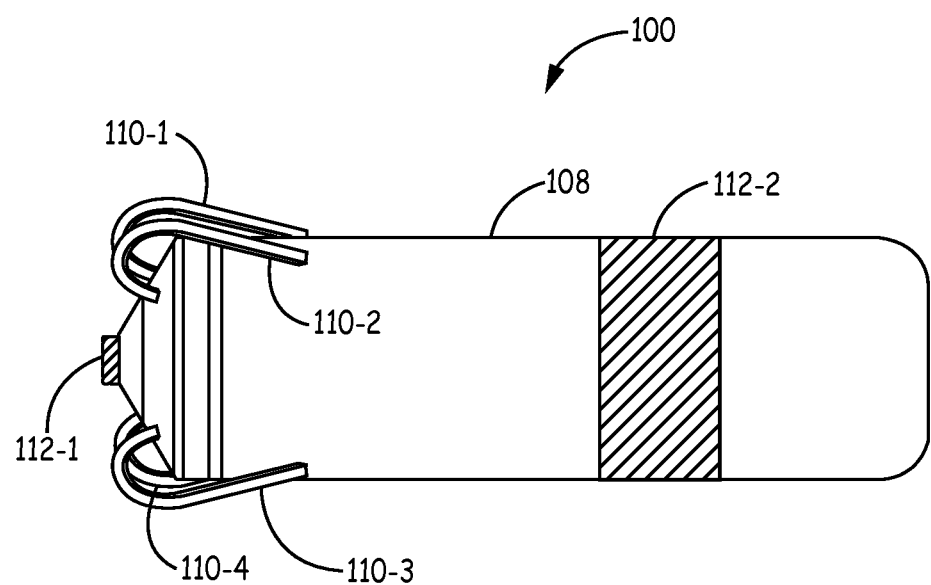
FIG. 1 shows an example leadless pacemaker device.

An implantable atrial pacemaker device of the present disclosure is configured for implantation within the atrium of a patient's heart. The atrial device may pace the atrium, sense intrinsic atrial electrical activity, and detect ventricular activation. The atrial device may control the timing of pacing pulses delivered to the atrium based on the detected atrial and ventricular activity.

The atrial device may include a hermetically sealed housing having a size and form factor that allows the atrial device to be implanted within the atrium. In some examples, the housing may have a cylindrical (e.g., pill-shaped) form factor. The housing may include fixation tines that connect the housing to the cardiac tissue within the atrium. The fixation tines may anchor the atrial device to the atrial cardiac tissue such that the atrial device moves along with the atrial cardiac tissue during cardiac contractions.

The housing of the atrial device may house components for sensing cardiac electrical activity such as intrinsic atrial depolarizations and ventricular depolarizations, e.g., far-field R-waves (FFRWs). The atrial device may also house components for delivering electrical stimulation therapy, such as pacing pulses. In some examples, the atrial device may also house components for sensing physiological parameters, such as acceleration, pressure, sound, and/or impedance.

The atrial device may include a plurality of electrodes used for sensing cardiac electrical activity and delivering electrical stimulation therapy (e.g., pacing pulses). For example, the atrial device may include a tip electrode and a ring electrode. The tip electrode may be located on the housing such that the tip electrode contacts the cardiac tissue when the atrial device is anchored to the cardiac tissue by the fixation tines. The ring electrode may also be located on the housing. For example, the ring electrode may be disposed around the circumference of the housing.

The atrial device may be configured to detect ventricular activation events. Ventricular activation may generally refer to electrical depolarization of the ventricular cardiac tissue and the subsequent mechanical contraction of the ventricular cardiac tissue. The atrial device may be configured to detect ventricular activation based on the detection of ventricular electrical activity and/or based on the detection of mechanical contraction of the ventricles. As used herein, detection of ventricular activation may generally refer to the detection of ventricular electrical activity (e.g., FFRWs) and/or the detection of mechanical contraction of the ventricles (e.g., based on heart sounds). In some examples, the atrial device may detect ventricular activation by detecting FFRWs. In some examples, the atrial device may detect ventricular activation by detecting S1 heart sounds. Although the atrial device may detect ventricular activation based on FFRWs and/or heart sounds, it is contemplated that the atrial device may detect ventricular activation using other sensors and techniques.

In some examples, the atrial device may detect FFRWs in the atrium, which are indicative of a ventricular depolarization. For example, the atrial device may detect FFRWs and determine when ventricular depolarization has occurred based on the detection of FFRWs. Although the atrial device is described herein as detecting ventricular depolarization based on the detection of FFRWs, the atrial device may also detect ventricular depolarization based on detected ventricular electrical activity other than FFRWs.

Additionally, or alternatively, the atrial device may be configured to detect mechanical contraction of the ventricles. For example, the atrial device may detect physiological parameters other than cardiac electrical activity, such as acceleration and/or pressure. In some examples, the atrial device may include one or more sensors that measure acceleration and/or pressure in the atrium. In these examples, the atrial device may detect mechanical contraction of the ventricles based on signals generated by the one or more sensors. For example, the atrial device may detect S1 heart sounds indicative of closure of the atrioventricular valves at the beginning of ventricular contraction and then determine that ventricular contraction has occurred based on the detection of S1 heart sounds. Additionally, or alternatively, the atrial device may detect S2 heart sounds in some examples, and then determine that ventricular contraction has occurred based on the detection of S2 heart sounds. In various embodiments, the atrial device may be configured to detect and use any combination of FFRWs, S1 heart sounds and/or S2 heart sounds.

The atrial device may control atrial pacing timing based on when ventricular activation is detected during a cardiac cycle. In some examples, the atrial device may determine when to pace the atrium based on when FFRWs are detected during the cardiac cycle. Additionally, or alternatively, the atrial device may determine when to pace the atrium based on when S1 heart sounds are detected during the cardiac cycle. A cardiac cycle may refer to cardiac electrical activity that occurs from the beginning of one heartbeat to the beginning of the next heartbeat, as sensed by electrodes and/or sensors of the atrial device. Components of the atrial device that sense cardiac electrical activity, sense contraction of the ventricles, and control the delivery of electrical stimulation to the atrium are described hereinafter.

The atrial device may include an electrical sensing module (i.e., sensing module) that is configured to monitor cardiac electrical activity in the atrium. The sensing module may include electronic components that acquire cardiac electrical signals via the electrodes of the atrial device (e.g., the tip and ring electrodes). In some examples, the sensing module may implement signal conditioning on the acquired electrical signals. For example, the sensing module may filter, amplify, and digitize the acquired electrical signals. The electrical activity monitored by the sensing module may include a variety of different electrical signal components. The electrical activity may include intrinsic cardiac electrical activity, e.g., intrinsic atrial activity and/or intrinsic ventricular electrical activity, or other electrical signals.

The atrial device may include one or more sensors, such as an accelerometer and/or a pressure sensor. An accelerometer included in the atrial device may generate signals that indicate the acceleration of the atrial device. A pressure sensor included in the atrial device may generate signals that indicate pressure within the atrium. When the atrial device includes a pressure sensor or an accelerometer, the atrial device may detect ventricular activation based on signals generated by the sensors. For example, as described above, the atrial device may detect contraction of the ventricles based on sensor signals indicative of ventricular contraction, such as S1 heart sounds.

The atrial device may include a stimulation generator module (i.e., "stimulation generator") that is configured to deliver electrical stimulation to the atrium via the electrodes (e.g., the tip and ring electrodes). For example, the atrial device may deliver pacing pulses to the atrium via the electrodes.

The atrial device may include a processing module that receives sensing data from the sensing module. The data received from the sensing module may include digitized electrical activity that was received via the electrodes of the atrial device. The processing module may detect intrinsic atrial activity based on the sensing data received from the sensing module. For example, the processing module may detect an intrinsic atrial depolarization based on the sensing data received from the sensing module. Detection of intrinsic atrial depolarization by the processing module may be referred to as an "atrial sensed event" or a "sensed atrial event" in some examples. Atrial electrical activity that is precipitated by delivery of a pacing pulse from the stimulation generator may be referred to as an "atrial paced event."

The processing module may detect ventricular activation events in a variety of different ways. In some examples, the processing module may detect ventricular electrical activity (e.g., FFRWs). If FFRWs are used, an algorithm may be used to discriminate atrial intrinsic events from FFRWs. In some examples, the processing module may detect ventricular contraction based on signals received from the one or more sensors included in the atrial device. For example, the processing module may detect heart sounds (e.g., the S1 heart sound) based on the signals received from the one or more sensors and detect ventricular contractions based on the detected heart sounds. Heart sounds may be mechanical perturbations generated during contractions of the heart, such as blood flow and the closing of heart valves. The sensors (e.g., acceleration and/or pressure sensors) may generate signals in response to the mechanical perturbations. Heart sounds may be referred to as S1, S2, S3, or S4 heart sounds, for example. The S1 heart sound may be caused by closure of the atrioventricular valves, e.g., the tricuspid and/or mitral valves at the beginning of ventricular contraction. As such, the S1 heart sound may indicate ventricular contraction. The processing module may also detect heart sounds S2, S3, and S4 in some examples, and determine other cardiac parameters based on the detected heart sounds.

As described above, the processing module may detect ventricular activation based on the detection of ventricular electrical activity (e.g., FFRWs) and/or based on the detection of other ventricular contractions (e.g., S1 heart sounds). In some examples, the processing module may detect ventricular activation based only on detected ventricular electrical activity. In other examples, the processing module may detect ventricular activation based only on the detection of ventricular contractions, e.g., based only on accelerometer data and/or pressure data. In still other examples, the processing module may detect ventricular activation based on a combination of both ventricular electrical activity and detected ventricular contractions, e.g., both FFRWs and S1 heart sounds.

The processing module may control when the stimulation generator delivers pacing pulses (i.e., atrial pacing timing) based on when the processing module detects atrial and ventricular activation during a cardiac cycle. For example, the processing module may first determine an amount of time between a ventricular activation event and a previous atrial event (e.g., an intrinsic or paced atrial event) that preceded the detected ventricular activation event. Then, the processing module may schedule a time at which to deliver a pacing pulse to the atrium based on the determined amount of time between the ventricular activation event and the previous atrial event. The processing module may then control the signal generator module to deliver the pacing pulse to the atrium at the scheduled time. In some examples, the processing module may be configured to inhibit delivery of a pacing pulse at the scheduled time if the processing module senses an intrinsic atrial depolarization before the scheduled time at which the pacing pulse was to be delivered.

The processing module may control atrial pacing timing based on the detection of ventricular activation in a variety of different ways. The manner in which the processing module controls atrial pacing timing may depend on when ventricular activation occurs relative to the atrial event that preceded (e.g., precipitated) the ventricular activation. For example, the manner in which the processing module controls atrial pacing timing may depend on when a FFRW is sensed relative to the atrial event that preceded the FFRW. As another example, the manner in which the processing module controls atrial pacing timing may depend on when an S1 heart sound is sensed relative to the atrial event that preceded the contraction causing the sensed S1 heart sound.

The atrial device of the present disclosure may operate as a stand-alone implantable device. In other words, the atrial device may operate as the sole pacing device implanted in the heart in some examples. Although the atrial device may operate as the sole pacing device implanted within the heart, in other examples, the atrial device may operate along with an implanted leadless ventricular pacemaker device. The ventricular device of the present disclosure may be implanted within a ventricle of the heart, sense ventricular depolarization, and pace the ventricle. The combination of the atrial and ventricular devices may be referred to herein as a leadless pacing system.

In some examples the atrial and ventricular devices may be implanted into the patient at the same time, e.g., during the same implant procedure. In other examples, the ventricular device may be implanted at a later time. For example, the patient may initially have the atrial device implanted to treat sick sinus syndrome (e.g., bradycardia), then have the ventricular device implanted at a later time after the patient develops AV block. In still other examples, the atrial device of the present disclosure may be implanted sometime after the ventricular device has already been implanted in an earlier procedure. For example, the atrial device may be implanted after the ventricular device if the patient develops pacemaker syndrome subsequent to implantation of the ventricular pacing device.

The atrial device of the present disclosure may operate reliably without modification when a ventricular device has been added to the patient's heart to form a leadless pacing system. Put another way, the atrial device of the present disclosure may not require modification (e.g., reprogramming) in order to function along with a subsequently implanted ventricular device. The atrial device may operate even when the ventricular device is added because the atrial device controls atrial pacing timing based on sensed ventricular activation, independent on the origin of the sensed ventricular activation. For example, the atrial device may control pacing timing in the manner described herein whether the ventricular activation detected by the atrial device arises due to intrinsic ventricular depolarization or due to ventricular pacing by the ventricular device. Accordingly, the atrial device of the present disclosure may function in a variety of different circumstances without modification, e.g., as a stand-alone device or implanted along with another device.

Although the atrial device of the present disclosure may not require additional programming upon implantation of a ventricular device, in some examples, the ventricular device may be programmed to function along with the atrial device in order to provide more optimal cardiac pacing. Put another way, in some examples, the ventricular device may be configured (e.g., programmed) to operate along with the atrial device in order to assure that the leadless pacing system performs at an optimal level. For example, the ventricular device may be configured to receive signals from the atrial device to increment its pacing rate, as described herein.

Figure 3:
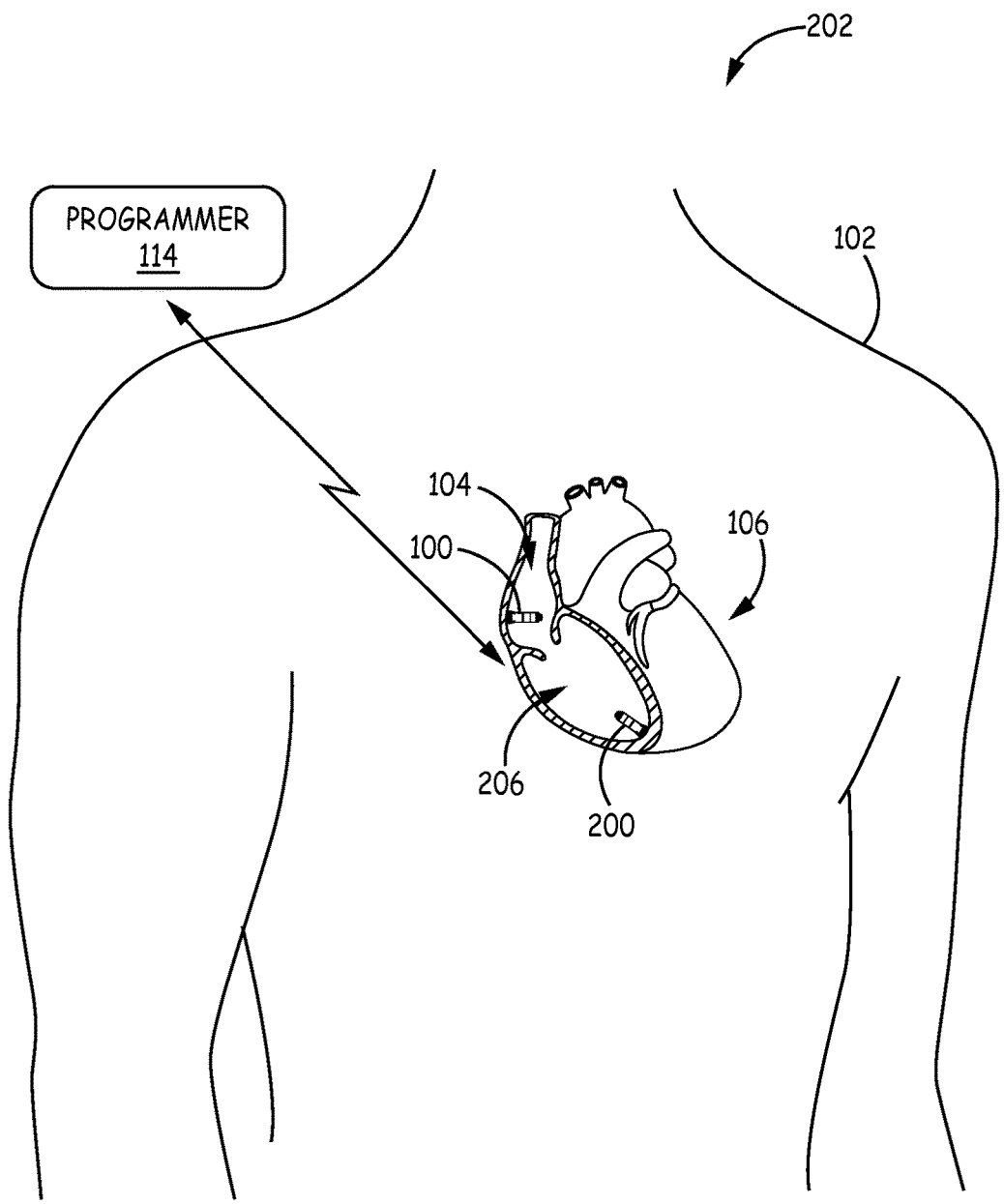
FIG. 3 shows an example leadless pacemaker system, including an atrial pacemaker device and a ventricular pacemaker device, implanted in a patient.

FIG. 1 shows a leadless atrial pacemaker device 100 (or "atrial device 100") that may be configured for implantation in a patient 102 (FIG. 3). For example, atrial device 100 may be configured for implantation within right atrium 104 of patient 102. Atrial device 100 may be configured to monitor electrical activity of heart 106 and/or provide electrical therapy to heart 106.

Atrial device 100 includes a housing 108, fixation tines 110-1, 110-2, 110-3, 110-4 (collectively "fixation tines 110"), and electrodes 112-1, 112-2. Housing 108 may have a pill-shaped cylindrical form factor in some examples. Fixation tines 110 are configured to connect (e.g., anchor) atrial device 100 to heart 106. Fixation tines 110 may be fabricated from a shape memory material, such as Nitinol. In some examples, fixation tines 110 may connect atrial device 100 to heart 106 within one of the chambers of heart 106. For example, as illustrated and described herein with respect to FIG. 3, fixation tines 110 may be configured to anchor atrial device 100 to heart 106 within right atrium 104. Although atrial device 100 includes a plurality of fixation tines 110 that are configured to anchor atrial device 100 to cardiac tissue in the right atrium, it is contemplated that a leadless device according to the present disclosure may be fixed to cardiac tissue in other chambers of a patient's heart using other types of fixation mechanisms.

Atrial device 100 may include one or more electrodes 112 for sensing electrical activity of heart 106 and/or delivering electrical stimulation to heart 106. Atrial device 100 includes two electrodes 112, although more than two electrodes may be included on an atrial device in other examples. Electrode 112-1 may be referred to as "tip electrode 112-1." Electrode 112-2 may be referred to as a "ring electrode 112-2." Tip electrode 112-1 and ring electrode 112-2 may be spaced apart a sufficient distance to be able to detect various electrical signals generated by the heart, such as P-waves generated by atria and FFRWs generated by ventricles. In one embodiment, for example, electrodes 112-1, 112-2 may be spaced at least 17 mm apart from one another. Fixation tines 110 may anchor atrial device 100 to cardiac tissue such that tip electrode 112-1 maintains contact with the cardiac tissue. Ring electrode 112-2 may be located on housing 108. For example, ring electrode 112-2 may be a cylindrical electrode that wraps around housing 108. Although ring electrode 112-2 is illustrated as a cylindrical electrode that wraps around housing 108, ring electrode 112-2 may include other geometries. In some examples, housing 108 may be formed from a conductive material. In these examples, housing 108 may act as an electrode of atrial device 100.

Housing 108 houses electronic components of atrial device 100. Electronic components may include any discrete and/or integrated electronic circuit components that implement analog and/or digital circuits capable of producing the functions attributed to atrial device 100 described herein. For example, housing 108 may house electronic components that sense electrical activity via electrodes 112 and/or deliver electrical stimulation via electrodes 112. Additionally, housing 108 may also include memory that includes instructions that, when executed by one or more processing circuits housed within housing 108, cause atrial device 100 to perform various functions attributed to atrial device 100 herein. Housing 108 may also house sensors that sense physiological conditions of patient 102, such as an accelerometer and/or a pressure sensor.

In some examples, housing 108 may house a communication module that enables leadless device 100 to communicate with other electronic devices, such as programmer 114 or other external patient monitor. In some examples, housing 108 may house an antenna for wireless communication. Housing 108 may also include a power source, such as a battery. Electronic components included within housing are described in further detail hereinafter.

Figure 2:
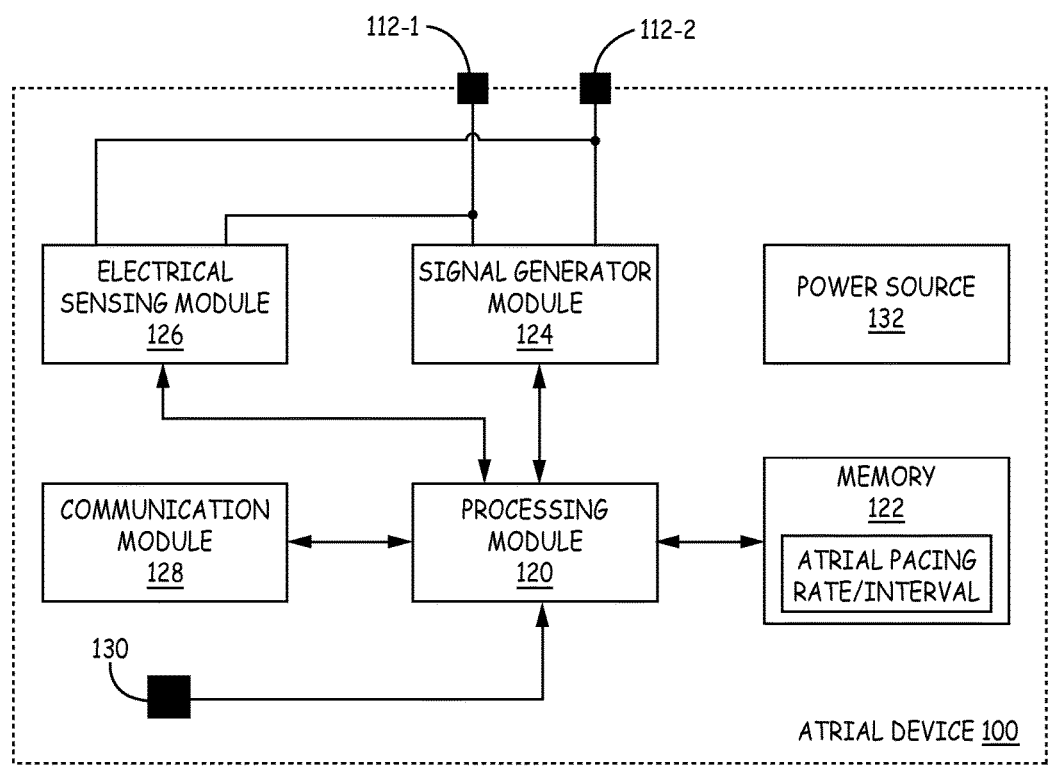
FIG. 2 is a functional block diagram of the example leadless pacemaker device.

FIG. 2 shows a functional block diagram of an example atrial device 100 configured for implantation within atrium 104 (FIG. 3). FIG. 3 shows a therapy system including atrial device 100 and programmer 114 that may be used to program atrial device 100 and retrieve data from atrial device 100. Atrial device 100 includes a processing module 120, memory 122, a signal generator module 124, an electrical sensing module 126, a communication module 128, a sensor 130, and a power source 132. Power source 132 may include a battery, e.g., a rechargeable or non-rechargeable battery.

Modules included in atrial device 100 represent functionality that may be included in atrial device 100 of the present disclosure. As discussed in U.S. Patent Application Pub. No. 2014/0121720, which was previously incorporated by reference, similar or identical modules and functionality may also be included in a ventricular pacemaker device, which may be provided as part of a dual-chamber, leadless pacemaker system for implantation and use in at least one atrium and at least one ventricle of a heart. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 120 may communicate with memory 122. Memory 122 may include computer-readable instructions that, when executed by processing module 120, cause processing module 120 to perform the various functions attributed to processing module 120 herein. Memory 122 may include any volatile, non-volatile, magnetic, or electrical media, such as RAM, ROM, NVRAM, EEPROM, Flash memory, or any other digital media. For example, memory 122 may include pacing instructions and values, such as the baseline atrial pacing rate, the baseline atrial pacing interval and the baseline AV interval. The pacing instructions and values may be updated by programmer 114 (FIG. 3). Pacing instructions included in memory 122 may cause atrial device 100 to operate as described in U.S. Patent Application Pub. No. 2014/0121720, which was previously incorporated by reference.

Processing module 120 may communicate with signal generator module 124 and electrical sensing module 126. Signal generator module 124 and electrical sensing module 126 are electrically coupled to electrodes 112. Electrical sensing module 126 is configured to monitor signals from electrodes 112 in order to monitor electrical activity of heart 106. Signal generator module 124 is configured to deliver electrical stimulation to atrium 104 via electrodes 112.

Processing module 120 may control signal generator module 124 to generate and deliver electrical stimulation to atrium 104 via electrodes 112. Electrical stimulation may include pacing pulses. Processing module 120 may control signal generator module 124 to deliver electrical stimulation therapy according to one or more atrial therapy programs including pacing instructions and values, which may be stored in memory 122.

Electrical sensing module 126 may include circuits that acquire electrical signals. Electrical signals acquired by electrical sensing module 126 may include intrinsic cardiac electrical activity, such as intrinsic atrial and/or intrinsic ventricular cardiac electrical activity. Electrical sensing module 126 may filter, amplify, and digitize the acquired electrical signals to generate raw digital data. Processing module 120 may receive the digitized data generated by electrical sensing module 126. In some examples, processing module 120 may perform various digital signal processing operations on the raw data, such as digital filtering.

Processing module 120 may sense cardiac events based on the data received from electrical sensing module 126. For example, processing module 120 may sense atrial events based on the data received from electrical sensing module 126. In some examples, processing module 120 may sense ventricular activation based on the data received from electrical sensing module 126. For example, processing module 120 may detect FFRWs indicative of ventricular activation based on the data received from electrical sensing module 126.

FIG. 3 shows an example leadless pacing system 202. Leadless pacing system 202 includes atrial device 100 and a leadless ventricular pacemaker device 200 (hereinafter "ventricular device 200"). Ventricular device 200 may be configured to pace the ventricle, sense intrinsic ventricular depolarizations, and inhibit ventricular pacing in response to detected ventricular depolarization. The structure of ventricular device 200 may be similar to the structure of atrial device 100. For example, ventricular device 200 may have a housing, fixation tines, and electrodes that are similar to housing 108, fixation tines 110, and electrodes 112 of atrial device 100 (FIG. 1).

Referring to FIG. 3, the fixation tines of ventricular device 200 are configured to connect (e.g., anchor) ventricular device 200 to heart 106. For example, the fixation tines of ventricular device 200 may be configured to anchor ventricular device 200 within the right or left ventricle. As illustrated and described herein with respect to FIG. 3, ventricular device 200 may be implanted within right ventricle 206.

Ventricular device 200 may include two or more electrodes (e.g., electrodes 222-1, 222-2 of FIG. 4) for sensing electrical activity of heart 106 and/or delivering electrical stimulation to heart 106. Ventricular device 200 may include a tip electrode and a ring electrode, similar to tip electrode 112-1 and ring electrode 112-2 of atrial device 100 (FIG. 1). The fixation tines of ventricular device 200 may anchor ventricular device 200 to cardiac tissue such that the tip electrode of ventricular device 200 maintains contact with the cardiac tissue.

Ventricular device 200 may include a housing that is similar to housing 108 of atrial device 100. The housing of ventricular device 200 houses electronic components of ventricular device 200. Electronic components may include any discrete and/or integrated electronic circuit components that implement analog and/or digital circuits capable of producing the functions attributed to ventricular device 200 described herein. For example, the housing of ventricular device may house electronic components that sense electrical activity via the electrodes of ventricular device 200 and/or deliver electrical stimulation via the electrodes of ventricular device 200. The housing of ventricular device may also include memory that includes instructions that, when executed by one or more processing circuits housed within the housing of ventricular device 200, cause ventricular device 200 to perform various functions attributed to ventricular device 200 herein. Ventricular device 200 may also include sensors that sense physiological conditions of patient 102, such as an accelerometer and/or a pressure sensor.

In some examples, ventricular device 200 may include a communication module that enables ventricular device 200 to communicate with other electronic devices, such as programmer 114. In some examples, ventricular device 200 may include an antenna for wireless communication with other devices. Ventricular device 200 may also include a power source, such as a battery.

Figure 4:
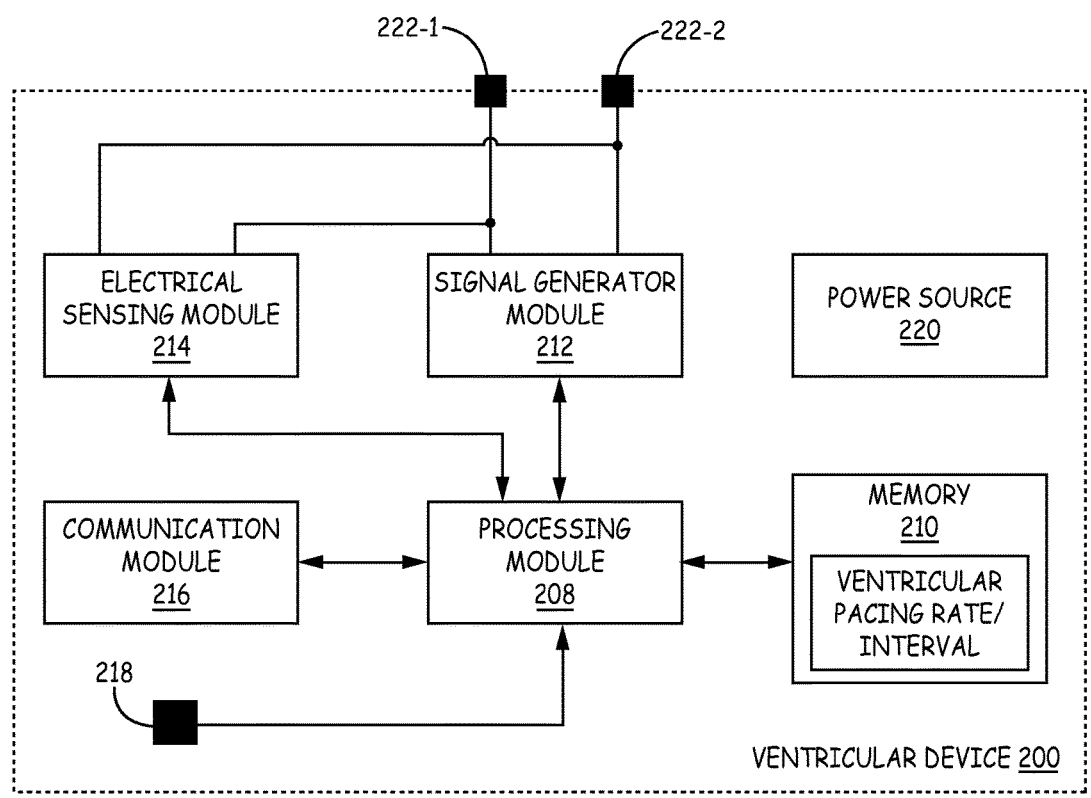
FIG. 4 is a functional block diagram of the example ventricular device.

FIG. 4 shows a functional block diagram of an example ventricular device 200 configured for implantation within ventricle 206. Ventricular device 200 includes a processing module 208, memory 210, a signal generator module 212, an electrical sensing module 214, a communication module 216, a sensor 218, and a power source 220. Power source 220 may include a battery, e.g., a rechargeable or non-rechargeable battery.

Processing module 208 may communicate with memory 210. Memory 210 may include computer-readable instructions that, when executed by processing module 208, cause processing module 208 to perform the various functions attributed to processing module 208 herein. Memory 210 may include any volatile, non-volatile, magnetic, or electrical media, such as RAM, ROM, NVRAM, EEPROM, Flash memory, or any other digital media. For example, memory 210 may include ventricular pacing instructions and values, such as a ventricular pacing rate, which may be updated by programmer 114. Ventricular pacing instructions included in memory 114 may cause ventricular device 200 to operate as described herein.

Processing module 208 may communicate with signal generator module 212 and electrical sensing module 214. Signal generator module 212 and electrical sensing module 214 are electrically coupled to electrodes 222-1, 222-2 (collectively "electrodes 222"). Electrical sensing module 214 is configured to monitor signals from electrodes 222 in order to monitor electrical activity of heart 106. Signal generator module 212 is configured to deliver electrical stimulation to heart 106 via electrodes 222. Processing module 208 may control signal generator module 212 to generate and deliver electrical stimulation to ventricle 206 via electrodes 222. Electrical stimulation may include pacing pulses. Processing module 208 may control signal generator module 136 to deliver electrical stimulation therapy according to one or more ventricular therapy programs that define a ventricular pacing rate. The ventricular therapy programs may be stored in memory 210.

Electrical sensing module 214 may include circuits that acquire electrical signals. Electrical signals acquired by electrical sensing module 214 may include intrinsic cardiac electrical activity, such as intrinsic ventricular depolarizations. Electrical sensing module 214 may filter, amplify, and digitize the acquired electrical signals to generate raw digital data. Processing module 208 may receive the digitized data generated by electrical sensing module 214. In some examples, processing module 208 may perform various digital signal processing operations on the raw data, such as digital filtering. Processing module 208 may sense ventricular events (e.g., intrinsic ventricular depolarizations) based on the data received from electrical sensing module 214.

Sensor 218 may comprise at least one of a variety of different sensors. For example, sensor 218 may comprise at least one of a pressure sensor and an accelerometer. Sensor 218 may generate signals that indicate an activity level of patient 102. Processing module 208 may detect an activity level of patient 102 based on the signals generated by sensor 218. The processing module 208 may use the signals generated by sensor 218 to determine the ventricular sensor rate.

Communication module 216 may include any suitable hardware (e.g., an antenna), firmware, software, or any combination thereof for communicating with another device, such as programmer 114 or a patient monitor. Under the control of processing module 208, communication module 216 may receive downlink telemetry from and send uplink telemetry to other devices, such as programmer 114 or a patient monitor, with the aid of an antenna included in communication module 216. As described herein, a leadless pacing system (e.g., leadless pacing system 202 of FIG. 3) may coordinate pacing of heart 106 based on sensed cardiac electrical and/or mechanical activity, with establishment of a communication link between atrial device 100 and ventricular device 200 on an as-needed basis to help maintain synchronous pacing of the heart. Accordingly, communication module 216 includes functionality that provides for communication between atrial device 100 and ventricular device 200. In some embodiments, ventricular device 200 may save power by turning on the portion of communication module 216 that receives signals from atrial device 100 only during periods when the ventricular device is delivering pacing pulses (i.e. when the AV node is blocked).

Ventricular device 200 may wirelessly communicate with programmer 114. For example, ventricular device 200 may transfer data to programmer 114 and may receive data from programmer 114. Programmer 114 may also wirelessly program ventricular device 200. For example, programmer 114 may wirelessly program operational parameters of ventricular device 200, such as the ventricular pacing rate.

In general, ventricular device 200 may be configured to pace ventricle 206 at a ventricular pacing rate. In the case where ventricular device 200 detects an intrinsic ventricular depolarization prior to delivering the pacing stimulus according to the ventricular pacing rate, ventricular device 200 may withhold stimulation. The ventricular pacing rate may be set such that ventricular device 200 tends to pace ventricle 206 in situations in which AV conduction is blocked. In other words, the ventricular pacing rate may be set at a rate that provides backup pacing to ensure that ventricle 206 is paced in situations where intrinsic ventricular depolarizations do not arise as a result of atrial depolarizations. In some examples, the ventricular backup pacing rate may be a rate that is relatively slow. For example, the ventricular pacing rate may be set to 50 ppm or may alternatively track a certain number of ppm below the ventricular intrinsic rate (for example, 10 ppm below the ventricular intrinsic rate). The ventricular device may be configured such that, after a specified number of ventricular paces at the backup rate, the ventricular pacing rate switches to the sensor rate determined by sensor 218 and processing module 208. The ventricular pacing rate may also be expressed as a ventricular pacing interval. The ventricular pacing interval may be the reciprocal value of the ventricular pacing rate.

Memory 210 may store the ventricular pacing rate and/or the ventricular pacing interval. In some examples, the ventricular pacing rate may initially be programmed into memory 210 upon initial implantation of ventricular device 200. The ventricular pacing rate may be updated in some examples. For example, a clinician may use programmer 114 to update the ventricular pacing rate. In some examples, processing module 208 may automatically update the ventricular pacing rate. For example, processing module 208 may determine an activity level of patient 102 and modify the ventricular pacing rate based on the activity level of patient 102. In this example, processing module 208 may increase the ventricular pacing rate upon determining that the patient activity level has increased. Processing module 208 may decrease the ventricular pacing rate upon determining that the patient activity level has decreased.

Processing module 208 may control signal generator module 212 to deliver pacing pulses at the ventricular pacing rate stored in memory 210. Processing module 208 may also inhibit the delivery of pacing pulses to ventricle 206 when processing module 208 detects an intrinsic ventricular depolarization. Accordingly, after a paced or sensed ventricular event, processing module 208 may schedule the next ventricular pacing pulse to occur such that the amount of time between the scheduled pacing pulse and the previous ventricular event is equal to the ventricular pacing interval.

As described above, the ventricular pacing rate may be set to a value that is less than the atrial pacing rate. In examples where the ventricular pacing rate is less than the atrial pacing rate and normal AV conduction is present in heart 106, ventricular device 200 may typically not pace ventricle 200. Instead, the pacing pulses delivered by atrial device 100 may cause intrinsic ventricular depolarizations that in turn cause ventricular device 200 to inhibit a scheduled ventricular pacing pulse. Accordingly, in the absence of AV block in heart 106, ventricular activation (e.g., FFRWs and S1 heart sounds) detected by atrial device 100 may typically arise due to intrinsic ventricular depolarizations.

Ventricular device 200 may pace ventricle 206 when AV block is present in heart 106. In some examples, AV block may be present temporarily in heart 106, e.g., for one or a few cardiac cycles. In other examples, AV block may persist for longer periods of time, or may be permanent. In examples where AV block occurs, the ventricular activation events (e.g., FFRWs and S1 heart sounds) detected by atrial device 100 may arise from paced ventricular events. In examples where AV block occurs temporarily between periods of AV conduction, the ventricular activations detected by atrial device 100 may arise from paced ventricular events during periods of AV block and may arise due to intrinsic ventricular depolarizations during periods of AV conduction. Accordingly, in one sense, the ventricular pacing rate of ventricular device 200 may be thought of as a backup pacing rate that causes ventricular device 200 to pace in circumstances where AV block occurs.

Figure 5:
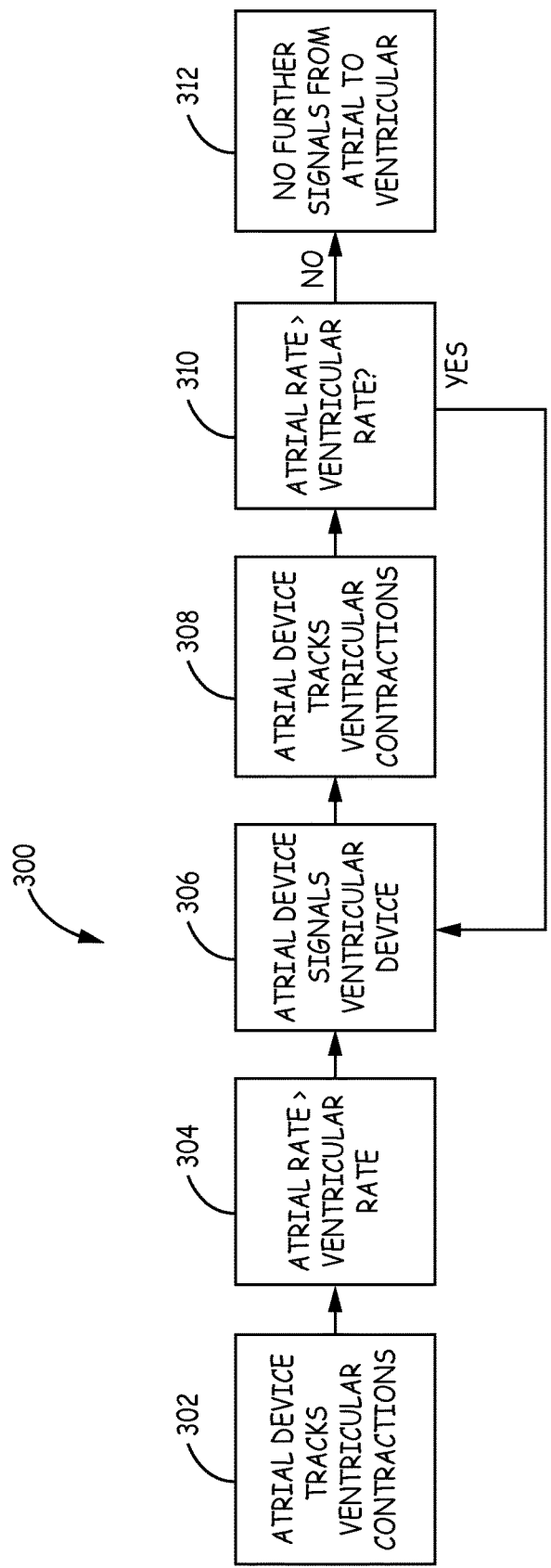
FIG. 5 is a flow diagram illustrating a method of timing the pacing of a dual-chamber leadless pacemaker system, according to one embodiment.

Referring now to FIG. 5, a method 300 for synchronizing atrial and ventricular pacemaker devices of a dual-chamber, leadless pacemaker system is illustrated. Method 300 may function primarily, though not necessarily, during AV block. Generally, in the dual-chamber, leadless pacemaker system, the atrial device tracks ventricular contractions 302, as described above. This tracking may be via FFRWs, heart sounds and/or other indicators of ventricular contraction. In the dual-chamber system described herein, tracking by the atrial device occurs whether there is AV block or not. If the atrial device detects that the atrial intrinsic contraction rate is less than the ventricular contraction rate, then the atrial device will pace the atrium according to timing determined by the measurement of the ventricular contraction rate. (For the purposes of this disclosure, the phrase "contraction rate" means the number of contractions during a time period, such as contractions per minute.) If the intrinsic atrial rate is faster than the ventricular contraction rate 304, on the other hand, the atrial and ventricular devices will eventually become out of synch, unless the ventricular pacing is corrected. Therefore, if the atrial rate is faster than the ventricular contraction rate 304, as might happen during AV block, for example, the atrial device sends a signal to the ventricular device 306 to increase its pacing rate. In some embodiments, this signal from the atrial pacemaker to the ventricular pacemaker may be sent only if at least a certain number or percentage of prior atrial beats were intrinsic beats. For example, the signal may only be sent, in one embodiment, if more than 15-20% of the prior atrial beats were intrinsic. The speed-up signal may be sent from the atrial device to the ventricular device via any suitable means, such as tissue conductance, radiofrequency, acoustic or other wireless signaling modalities.

The signal from the atrial device to the ventricular device may instruct the ventricular device to increase its pacing rate by any suitable amount. In some cases, the ventricular device may increase its rate in equal increments with each signal received from the atrial device. For example, the ventricular device may increase its rate in increments of 5 ppm or 10 ppm with each received signal. In other embodiments, the ventricular device may increase its rate in unequal increments. For example, in one embodiment, the ventricular device may increase its rate in increments of 10 ppm up to a certain rate, such as 80 ppm, and may then increase its rate in increments of 5 ppm for every signal received thereafter. In other embodiments, the ventricular device may have predetermined pacing rates, and upon receiving a signal from the atrial device, the ventricular device may speed up to the next highest rate. For example, the ventricular device may be pacing at a rate of 72 ppm when it receives a signal, and the next highest rate may be 75 ppm, so the ventricular device changes its rate from 72 ppm to 75 ppm. The next level may be 80 ppm, so if the ventricular device receives another signal from the atrial device, it will increase its rate from 75 ppm to 80 ppm. Such predetermined rates may be based on ppm or may be quantized levels based on ppm, beats per minute, millisecond intervals and/or other criteria. In various alternative embodiments, any increments, decrements or combinations of increments and decrements may be used by a dual-chamber, leadless pacemaker system described herein.

After the atrial device has signaled the ventricular device to increase its rate 306, the atrial device continues to track the ventricular contractions 308. If the atrial intrinsic rate is still greater than the ventricular rate 310, then the atrial device will send another signal to the ventricular device 306 to speed up. This process may be repeated as many times as necessary to bring the ventricular rate to a level that exceeds the atrial intrinsic rate. In some embodiments, the ventricular device may be configured to increase only to a certain threshold level and not increase beyond that level. For example, a threshold level may be set at about 120-130 beats per minute, so the ventricular device will not exceed that pacing rate. If the atrial rate no longer exceeds the ventricular rate, then the atrial device will not send any additional signals to the ventricular device 312. In some embodiments, the atrial device will send one or more signals to the ventricular device 306, and the ventricular rate will adjust to a level that is higher than the atrial rate. The atrial pacemaker device will detect the ventricular contractions 308 and increase its own atrial pacing rate to match the new, increased ventricular rate. In at least some embodiments, an atrial rate and a ventricular rate will be higher than the atrial intrinsic rate, so that the atrial device will operate at 100% pacing, rather than the atrium beating at its intrinsic rate.

The ventricular device may be configured so that after a predetermined amount of time, if it has not received a signal from the atrial device, it will decrease its pacing rate. The decrease in the ventricular pacing rate may be to the ventricular sensor rate or to some other, predetermined level. The ventricular device may decrease its rate in decrements over time, and these decrements may be the same as the increments used to increase the rate or may be different decrements. For example, in some embodiments, the ventricular device may be configured to increase its rate in increments that are larger than decrements at which it decreases its rate. In one embodiment, for example, the ventricular device may increase its rate in increments of 10 ppm and decrease its rate in decrements of 5 ppm. Any of the increments described above for increases in ventricular rate may also be applied to decrements for decreases in the rate.

Various examples have been described. These and other examples are within the scope of the following claims.

The invention claimed is:

1. A method for adjusting a pacing rate in a dual-chamber, leadless pacemaker system implanted in a heart, the method comprising:
   sensing, with a sensor in a leadless atrial pacemaker implanted in an atrium of the heart, a first far-field R-wave indicating a depolarization of a ventricle of the heart;
   determining, with a processor in the leadless atrial pacemaker and based on the sensed first far-field R-wave that an intrinsic atrial contraction rate of the atrium is faster than a ventricular contraction rate;
   transmitting a first signal from the atrial pacemaker to a leadless ventricular pacemaker implanted in a ventricle of the heart to increase a ventricular pacing rate of the ventricular pacemaker;
   receiving the transmitted first signal with the ventricular pacemaker;
   increasing the ventricular pacing rate, based on the received first signal;
   determining, with the ventricular pacemaker, that no signal has been received from the atrial pacemaker for a predetermined amount of time; and
   decreasing the ventricular pacing rate.

2. The method of claim 1, further comprising, after the transmitting step:
   sensing a second far-field R-wave with the sensor;
   determining, with the processor and based on the sensed second far-field R-wave that the intrinsic atrial contraction rate is still faster than the ventricular contraction rate;
   transmitting a second signal from the atrial pacemaker to the ventricular pacemaker to increase the ventricular pacing rate;
   receiving the transmitted second signal with the ventricular pacemaker; and
   increasing the ventricular pacing rate, based on the received second signal.

3. The method of claim 2, further comprising repeating the sensing, determining, transmitting, receiving and increasing steps, until the ventricular contraction rate exceeds the intrinsic atrial contraction rate.

4. The method of claim 3, further comprising:
   determining, with the atrial pacemaker, that the ventricular contraction rate exceeds the intrinsic atrial rate; and
   sending pacing pulses from the atrial pacemaker to the atrium to cause the atrium to contract at an atrial pacing rate that approximates the ventricular contraction rate.

5. The method of claim 1, further comprising:
   determining, with the ventricular pacemaker, that a threshold ventricular pacing rate has been reached; and
   discontinuing any further increases in the ventricular pacing rate.

6. The method of claim 1, wherein decreasing the ventricular pacing rate comprises decreasing the ventricular pacing rate by a predetermined decrement of at least 2 pulses per minute (ppm) and not more than 10 ppm.

7. The method of claim 1, wherein increasing the ventricular pacing rate comprises increasing the ventricular pacing rate by a predetermined increment of at least 2 pulses per minute (ppm) and not more than 10 ppm.

8. The method of claim 1, wherein increasing the ventricular pacing rate comprises increasing the ventricular pacing rate from a current rate to a next higher predetermined level of pacing rates.

9. A non-transitory, computer-readable storage medium storing a set of instructions that cause a dual-chamber, leadless pacemaker system implanted in a heart to perform a method, the method comprising:
   sensing, with a sensor in a leadless atrial pacemaker implanted in an atrium of the heart, a first far-field R-wave indicating a depolarization of a ventricle of the heart;
   determining, with a processor in the leadless atrial pacemaker and based on the sensed first far-field R-wave that an intrinsic atrial contraction rate of the atrium is faster than a ventricular contraction rate;
   transmitting a first signal from the atrial pacemaker to a leadless ventricular pacemaker implanted in a ventricle of the heart to increase a ventricular pacing rate of the ventricular pacemaker;
   receiving the transmitted first signal with the ventricular pacemaker;
   increasing the ventricular pacing rate, based on the received first signal;
   determining, with the ventricular pacemaker, that no signal has been received from the atrial pacemaker for a predetermined amount of time; and
   decreasing the ventricular pacing rate.

10. The storage medium of claim 9, wherein the method further comprises, after the transmitting step:
    sensing a second far-field R-wave with the sensor;
    determining, with the processor and based on the sensed second far-field R-wave that the intrinsic atrial contraction rate is still faster than the ventricular contraction rate;
    transmitting a second signal from the atrial pacemaker to the ventricular pacemaker to increase the ventricular pacing rate;
    receiving the transmitted second signal with the ventricular pacemaker; and
    increasing the ventricular pacing rate, based on the received second signal.

11. The storage medium of claim 10, wherein the method further comprises repeating the sensing, determining, transmitting, receiving and increasing steps until the ventricular contraction rate exceeds the intrinsic atrial contraction rate.

12. The storage medium of claim 11, wherein the method further comprises:
    determining, with the atrial pacemaker, that the ventricular contraction rate exceeds the intrinsic atrial rate; and
    sending pacing pulses from the atrial pacemaker to the atrium to cause the atrium to contract at an atrial pacing rate that approximates the ventricular contraction rate.

13. The storage medium of claim 9, wherein increasing the ventricular pacing rate comprises increasing the ventricular pacing rate by a predetermined increment of at least 2 pulses per minute (ppm) and not more than 10 ppm.

14. The storage medium of claim 9, wherein increasing the ventricular pacing rate comprises increasing the ventricular pacing rate from a current rate to a next higher predetermined level of pacing rates.

15. An implantable, dual-chamber, leadless pacemaker system, comprising:
    an atrial leadless pacemaker, comprising:
       a sensing module configured to sense signals indicative of ventricular contractions;

a processing module configured to determine whether an intrinsic atrial contraction rate is greater than a ventricular contraction rate; and a communication module configured to transmit a signal to a ventricular leadless pacemaker to increase a ventricular pacing rate in response to instructions from the processing module to increase the ventricular pacing rate; and a ventricular leadless pacemaker, comprising:

a sensing module configured to receive the transmitted signal from the atrial pacemaker; and a processing module configured to increase the ventricular pacing rate according to the received signal, to determine when no signal has been received from the atrial pacemaker for a predetermined amount of time, and to decrease the ventricular pacing rate when no signal has been received from the atrial pacemaker for the predetermined amount of time, wherein the processing module of the atrial pacemaker is further configured to begin pacing the atrium at an atrial pacing rate that is faster than the intrinsic atrial contraction rate and that at least approximately matches the ventricular pacing rate.

16. The system of claim 15, wherein the sensing module of the atrial pacemaker is configured to sense at least one of far-field R-waves or heart sounds.

17. The system of claim 15, wherein the processing module of the atrial pacemaker is further configured to determine that the ventricular contraction rate exceeds the intrinsic atrial contraction rate and to discontinue transmission of signals from the atrial pacemaker to the ventricular pacemaker.

18. The system of claim 15, wherein the processing module of the ventricular pacemaker is configured to increase the ventricular pacing rate by a predetermined increment and decrease the ventricular pacing rate by a predetermined decrement that is less than the predetermined increment.

19. The system claim 15, wherein the processing module of the ventricular pacemaker is configured to increase and decrease the ventricular pacing rate between predetermined, quantized levels.

20. The system of claim 15, wherein the processing module of the ventricular pacemaker is further configured to determine that a threshold ventricular pacing rate has been reached and to discontinue increasing the ventricular pacing rate.

* * * * *